(12) United States Patent
Weig

(10) Patent No.: US 8,939,952 B2
(45) Date of Patent: *Jan. 27, 2015

(54) SEAL FOR A RECTAL OR OSTOMY APPLIANCE

(75) Inventor: Bret Weig, Browns Mills, NJ (US)

(73) Assignee: Convatec Technologies Inc., Las Vegas, NV (US)

( * ) Notice: Subject to any disclaimer, the term of this patent is extended or adjusted under 35 U.S.C. 154(b) by 361 days.

This patent is subject to a terminal disclaimer.

(21) Appl. No.: 12/527,716

(22) PCT Filed: Feb. 21, 2008

(86) PCT No.: PCT/US2008/054517
§ 371 (c)(1),
(2), (4) Date: Aug. 19, 2009

(87) PCT Pub. No.: WO2008/103788
PCT Pub. Date: Aug. 28, 2008

(65) Prior Publication Data
US 2010/0022976 A1    Jan. 28, 2010

Related U.S. Application Data

(60) Provisional application No. 60/891,120, filed on Feb. 22, 2007, provisional application No. 60/891,127, filed on Feb. 22, 2007.

(51) Int. Cl.
*A61F 5/458* (2006.01)
*A61M 25/10* (2013.01)
(Continued)

(52) U.S. Cl.
CPC ............. *A61F 5/445* (2013.01); *A61F 2/0027* (2013.01)
USPC ..................... 604/355; 604/101.05

(58) Field of Classification Search
CPC .............................. A61F 5/445; A61F 2/0027
USPC .......... 604/101.05, 355, 101.01, 919, 103.03, 604/103.07, 103.08
See application file for complete search history.

(56) References Cited

U.S. PATENT DOCUMENTS 2,078,686 A * 4/1937 Rowe ..................... 604/103.02
2,499,045 A * 2/1950 Walker et al. ............ 604/103.02
(Continued)

FOREIGN PATENT DOCUMENTS

DE     102004033425     7/2006
JP         9253112       9/1997
(Continued)

OTHER PUBLICATIONS

Machine translation of Japanese Patent Document JP 10-234854 to Shigenobu, 1998.*

*Primary Examiner* — Melanie Hand
*Assistant Examiner* — Paula L Craig
(74) *Attorney, Agent, or Firm* — Lorelei P. Westin

(57) ABSTRACT

A rectal appliance with a tubular member defining a communication passage for body waste, and first and second inflatable chamber portions carried on the tubular member for forming internal and external seals with respect to the anus. One or both of the inflatable chamber portions have a partly flared shape. The second inflatable chamber portion has a low external profile, and a concave sealing surface. The inflatable chamber portions are defined at least partly by a common flexible membrane that is constrained near a middle region to define a narrow waist between the two inflatable chamber portions.

21 Claims, 3 Drawing Sheets

(51) Int. Cl.
*A61F 5/445* (2006.01)
*A61F 2/00* (2006.01)

(56) References Cited

U.S. PATENT DOCUMENTS

| | | | |
|---|---|---|---|
| 2,610,626 A | 9/1952 | Edwards | |
| 3,154,077 A * | 10/1964 | Cannon | 606/192 |
| 3,459,175 A * | 8/1969 | Miller | 600/431 |
| 3,459,178 A | 8/1969 | Miller | |
| 3,509,884 A * | 5/1970 | Bell | 604/101.05 |
| 3,630,206 A * | 12/1971 | Gingold | 604/103.08 |
| 3,765,413 A | 10/1973 | Lepar | |
| 3,915,171 A * | 10/1975 | Shermeta | 604/101.05 |
| 4,019,515 A * | 4/1977 | Kornblum et al. | 604/101.05 |
| 4,555,242 A * | 11/1985 | Saudagar | 604/103.08 |
| 4,650,463 A * | 3/1987 | LeVeen et al. | 604/43 |
| 4,686,985 A | 8/1987 | Lottick | |
| 4,705,502 A * | 11/1987 | Patel | 604/544 |
| 4,850,953 A * | 7/1989 | Haber et al. | 600/32 |
| 4,941,877 A * | 7/1990 | Montano, Jr. | 604/103.07 |
| 5,074,845 A * | 12/1991 | Miraki et al. | 604/103.08 |
| 5,195,970 A * | 3/1993 | Gahara | 604/103.08 |
| 5,312,343 A * | 5/1994 | Krog et al. | 604/101.03 |
| 5,312,384 A | 5/1994 | Temple | |
| 5,342,301 A * | 8/1994 | Saab | 604/103.13 |
| 5,415,634 A * | 5/1995 | Glynn et al. | 604/103.08 |
| 5,458,572 A * | 10/1995 | Campbell et al. | 604/103.08 |
| 5,545,132 A * | 8/1996 | Fagan et al. | 604/103.08 |
| 5,620,457 A * | 4/1997 | Pinchasik et al. | 606/194 |
| 6,129,706 A * | 10/2000 | Janacek | 604/103.08 |
| 6,249,708 B1 * | 6/2001 | Nelson et al. | 607/122 |
| 6,296,655 B1 * | 10/2001 | Gaudoin et al. | 606/194 |
| 6,527,755 B1 * | 3/2003 | Salama | 604/348 |
| 6,544,224 B1 * | 4/2003 | Steese-Bradley | 604/103.06 |
| 8,388,586 B2 * | 3/2013 | Weig | 604/338 |
| 2005/0033226 A1 * | 2/2005 | Kim | 604/101.01 |
| 2006/0079838 A1 * | 4/2006 | Walker et al. | 604/104 |
| 2007/0213661 A1 * | 9/2007 | Gobel | 604/96.01 |
| 2008/0262449 A1 * | 10/2008 | Shah et al. | 604/339 |
| 2009/0043151 A1 * | 2/2009 | Gobel | 600/31 |
| 2010/0069859 A1 * | 3/2010 | Weig | 604/335 |

FOREIGN PATENT DOCUMENTS

| | | |
|---|---|---|
| JP | 10-234854 | 9/1998 |
| WO | 2006010556 | 2/2006 |

* cited by examiner

SEAL FOR A RECTAL OR OSTOMY APPLIANCE

This application is a national phase application of PCT/US08/54517 filed Feb. 21, 2008, and claims priority to U.S. Provisional Application Nos. 60/891,120 filed Feb. 22, 2007 and 60/891,127 filed Feb. 22, 2007.

FIELD OF THE INVENTION

The present invention relates to the field of rectal appliances, for fitting to a person's anus. One aspect of the invention relates to the formation of a seal around the anus.

BACKGROUND TO THE INVENTION

When a person loses sphincter control, intervention with some sort of rectal, continence control appliance is often employed. Creating a seal around the anus such that the seal is dependable and conducive to body tissue is important for the function of continence control devices. Once this seal has been made, a variety of techniques may be employed for containing, collecting and/or controlling stool. Some current devices rely on adhesives to attempt to create a seal between the appliance and the anus. However, an adhesive seal can affect, and can be affected by, the wearer's mobility. Should the adhesive seal fail, then the wearer may be exposed to uncontrolled discharge of stool. Other devices use an expandable balloon or other expandable member to form a single seal against the inside of the body opening, or may use plastic or other materials to form a rigid shape for insertion. Again, such seals can affect, and can be affected by, the wearer's mobility. Also, such devices have to be designed carefully to avoid the risk of damage to the sensitive internal tissue. A relatively high concentration of force may result on the tissue underneath the body opening, especially when the external surface or stop is of limited conformability.

By way of example, reference is made to JP-A-9253112 which describes a rectal appliance with a discharge tube carrying internally fitting and externally fitting inflatable balloons. Such a device may reduce the risk of tissue damage by using inflatable balloons internally and externally of the anus to sandwich the anus. However, the device is bulky, which may make it impractical to wear for extended periods, or under normal clothing. For example, the size and shape of the external balloon is extremely prohibitive without benefiting the seal performance.

U.S. Pat. No. 4,686,985 describes an anal dilator and occluder also including internally fitting and externally fitting inflatable balloons. The device has an asymmetric shape suited to the shape of the anus. However, the device is merely an occluding plug and does not permit any discharge of stool when in position. The device has to be removed in order to defacate. Not only is this inconvenient, but it also involves frequent handling of the device which is potentially unhygienic.

SUMMARY OF THE INVENTION

One aspect of the invention is to provide a seal for a rectal appliance. The seal optionally comprises a first (internal) inflatable chamber portion for sealing against the internal wall of the rectum. The seal comprises a second (external) inflatable chamber portion for sealing against the perianal tissue.

The appliance further comprises a discharge passage extending through the first and second inflatable chamber portions. The appliance permits discharge of stool from the anus without having to remove the appliance entirely. The discharge passage is defined by a tubular member passing through each inflatable chamber portion.

The appliance includes one or more of the following features relating to its shape and/or construction:

(a) The second or external inflatable chamber portion may, when inflated, have a generally flared shape, a trumpet shape, a concave shaped sealing surface, and/or conform to the shape of the body. Such a shape enables a better fit to be achieved externally than, for example, a doughnut-shape. It also provides a greater external sealing area, and thus reduces pressure concentration.

(b) The second or external inflatable chamber portion comprises a first flexible wall portion attached, for example, at a seam to a second flexible wall portion. The seam extends around a periphery of the second inflatable chamber portion. Such a construction enables the shape of the second inflatable chamber portion to be controlled. In the region of the seam, the second inflatable chamber portion swells in the shape of a pouch, rather than like a bulb. The second inflatable wall may be of a thicker material than the first flexible wall portion to provide increased protection against punctures. The second inflatable wall may also be made of an elastic material that once the device is inflated may be stretched to provide a pressure and/or volumetric reserve which may assist with keeping the first and second chambers at a set pressure and/or provide an elastic rebound, and to more easily allow volumetric changes to occur between the chambers.

(c) The second or external inflatable chamber portion may comprise a molded rear wall. The molded rear wall may define a predetermined shape, for example, non-bulbous. By using such a molded rear wall, a rear or externally facing portion of the second inflatable chamber portion may have a generally flat profile, or at least low profile. This can provide a more compact design than if the second chamber portion has a bulbous doughnut shape.

(d) The first and second chamber portions may be defined at least partly by a common flexible membrane material secured around a tubular support. The membrane material may have a waist or neck defined by a region at which the membrane material is secured to the tubular support, at a point between the first and second chamber portions. The tubular support may partly define a wall or surface of at least one of the first and second chamber portions. One or more communication channels may be defined between the first and second chamber portions, for example, at the waist. The communication channels or passageways are comprised of a plurality of spaced, parallel axial bonds, to define a corrugated shape. In one embodiment these corrugations may take the form of structurally inflatable columns that together act as the tubular support or stem itself, replacing it, in effect creating an inflatable stem.

Although the first inflatable chamber portion has been mentioned above, this might not be essential in all definitions and embodiments of the invention.

As used herein, the term "inflatable" means a chamber portion that is configured to be expanded by inflating the chamber with a positive inflation pressure (e.g., a pressure of inflation fluid greater than the external pressure).

DETAILED DESCRIPTION OF PREFERRED EMBODIMENT

Figure 1:
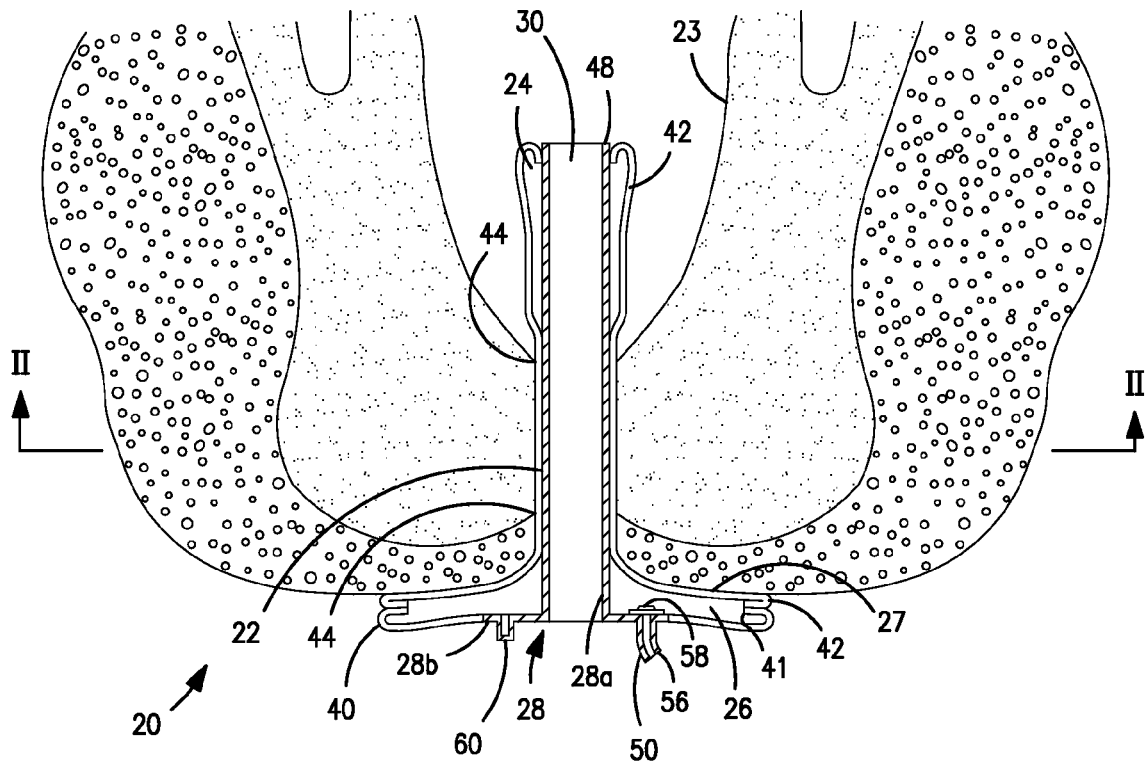
FIG. 1 is a schematic sectional view of a rectal appliance in a non-inflated condition.

Referring to the drawings, a rectal appliance 20 comprises an inflatable seal for sealing around the anus 22 of an incontinent person.

The rectal appliance 20 generally comprises a first (or internal) inflatable chamber portion 24 for insertion in the anus 22 to seal against the inside wall of the anus 22 and the rectal lumen 23. The first inflatable chamber portion 24 has a generally closed-loop or cuff form. The rectal appliance 20 may further comprise a second (or external) inflatable chamber portion 26 for forming an external seal against the anus 22 and against the perianal skin 27. The second inflatable chamber portion 26 has a generally closed-loop or cuff form.

The first and second inflatable chamber portions 24, 26 are carried on and/or at least partly defined by a support (tubular member) 28 comprising a tubular stem 28a. The support 28 further comprises a flange-like base 28b projecting from the stem 28a. The base 28b supports a flexible rear wall 40 which itself is attached to a flexible membrane 42 at a seam 41. The flexible rear wall 40 is a closed loop shape, and the seam 41 has a generally closed-loop shape, for example, annular or circular. The seam 41 may project inwardly or outwardly. The flexible membrane 42 may have a different material characteristic from the rear wall 40. For example, the materials may be different, and/or of different thickness, flexibility or elasticity and/or have different strengths. In the current embodiment, the flexible membrane 42 is of a thinner material than the rear wall 40, since the flexible membrane 42 is desired to be highly conformable for sealing around the anus 22. Also, since the rear wall 40 faces outwards in use, using a thicker material for the rear wall 40 also provides greater strength and protection against punctures. The rear wall 40 may also be constructed of elastic material or contain within it elastic material that may provide a volumetric reserve and/or an elastic rebound to the device.

Figure 2:
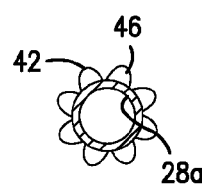
FIG. 2 is a schematic sectional view along the line 11-11 of FIG. 1 showing only the details of the appliance.
Figure 4:
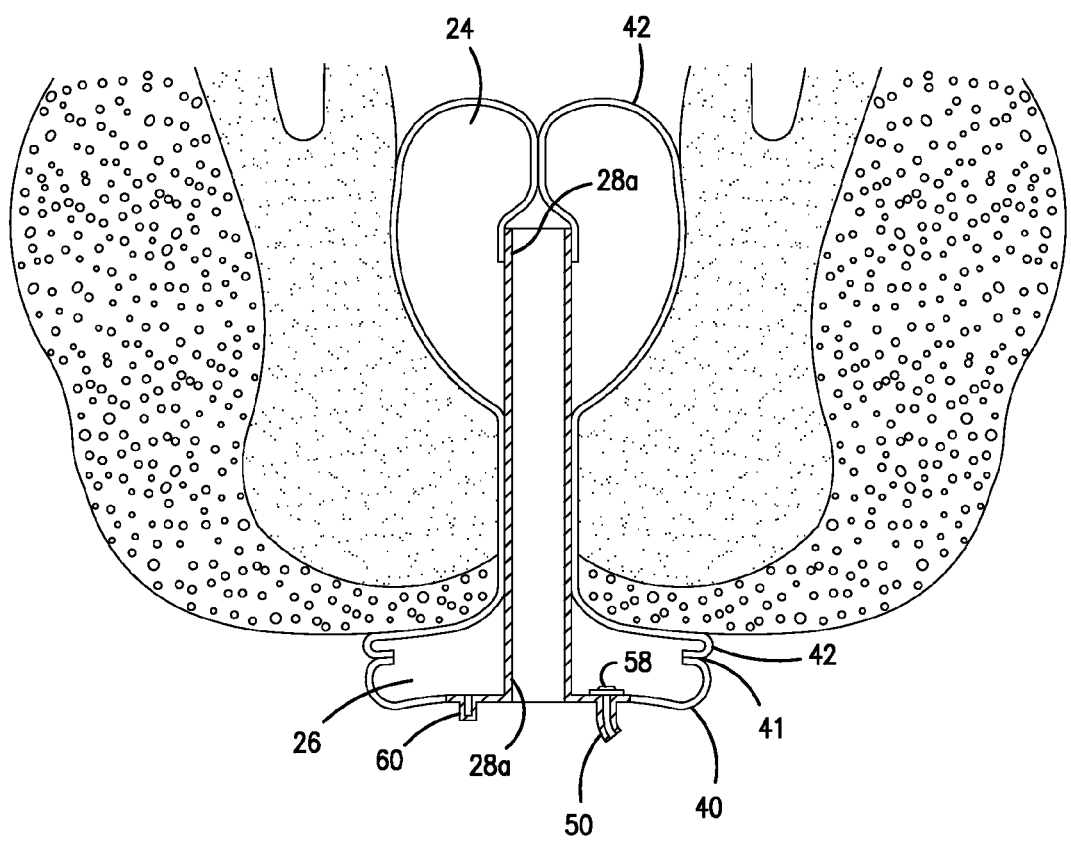
FIG. 4 is a sectional view of another embodiment pf a rectal appliance with a closure according to the present invention.

The opposite end of the flexible membrane 42 is attached at or near a distal end 48 of the stem 28a. In one embodiment the flexible membrane 42 may have sufficient material within the rectal chamber so when inflated the first chamber 24 forms a closure in front of the distal end 48 of the stem 28a as shown in FIG. 4. This closure is opened to discharge waste by partially deflating and/or reducing the pressure within the device but retaining enough to maintain the device in place. The flexible membrane 42 may be striated near a middle region 44 of the stem 28a, (e.g., attached to the stem 28a along a plurality of spaced, parallel axial bonds, to define a corrugated shape shown in FIG. 2, with parallel narrow connecting pathways 46 between the stem 28a and the membrane 42). In FIG. 2, the size of the connecting pathways 46 are exaggerated for clarity. The connecting pathways 46 not only act as a fluidic connection between the first and second chambers 24, 26, but with varying the size and shape of the corrugations may also act as a cushion against the inner wall of the rectum. They may also act to: (i) reduce the friction between the stem 28a and the inner wall of the rectum: (ii) restrict flow between the first and second chambers 24, 26 providing a damping effect to the volumetric changes between the chambers 24, 26; (iii) provide structurally inflatable columns that together act as the stem in the embodiment where the stem is inflatable; (iv) provide pathways for flatus to more easily escape between the corrugations and the inner wall of the rectum in the embodiment where the rectum opening is normally closed and flatus escapes around the outside of the first and second chambers 24, 26 as shown in FIG. 4. Other forms of discontinuous seal may also be used to define one or more connecting pathways 46 in a similar manner.

The combination of the stem 28a (from the middle region 44 to the distal end 48) and the flexible membrane 42 (extending from the distal end 48 to the middle region 44 of the stem 28a) defines the first inflatable chamber portion 24. The combination of the base 28b, the stem 28a (down to the middle region 44), the flexible rear wall 40 and the flexible membrane 42 defines the second inflatable chamber portion 26. The first and second chamber portions 24, 26 communicate via connecting pathways 46 created by the striations at the middle region 44 of the stem 28a). A neck or waist 25 is defined between the first and second inflatable chamber portions 24, 26 at the striations.

Such a construction can enable the appliance to be manufactured easily and efficiently, without having to provide separate inflatable balloons for each inflatable chamber portion.

In use, the first and second chamber portions 24, 26 are initially deflated. The user presents the distal end portion 48 of the stem 28a to the anus 22 and inserts the stem 28a partway, in order to insert at least a portion of the first inflatable chamber 24 (FIG. 1). For example, the distal end portion 48 may be inserted using a dedicated introducer tool, such as described in U.S. Patent Publication No. 2005054996 or U.S. Patent Publication No. 2005137526, and the distal end portion 48 may include any suitable adaptations for use with such a tool. Thereafter, the first and second chamber portions 24, 26 are inflated (FIG. 3) by connecting an inflation source (not shown) to an inflation port 50 formed in the base 28b. For a rectal appliance 20, the inflation port 50 may typically comprise a tube 56 extending from the rectal appliance 20 to a remote point that the user will find easily accessible. The inflation port 50 may include a non-return valve 58. Any suitable inflation fluid may be used, for example, a gas (such as air), or a liquid (such as saline). The inflation source may, for example, comprise a syringe, a pump (for example, an electric or manual pump), or an oral inflation tube.

In the present embodiment, the first and second inflatable chamber portions 24, 26 are inflated in common with each other, by virtue of the connecting pathways 46 near the middle region 44 of the stem 28a. In an alternative embodiment, the striations could be replaced by a continuous annular or band weld, and one or more separate communication lumens or tubes may be provided for communication of inflation fluid between the two inflatable chamber portions 24, 26, or from the inflation port 50. Alternatively, the first and second chamber portions 24, 26 may not communicate with each other, and each inflatable chamber portion 24, 26 may be inflated independently via its own respective inflation port (not shown).

As the first and second inflatable chamber portions 24, 26 swell, the rectal appliance 20 may self-locate with respect to the anus 22. Even if the middle region 44 of the stem 28a might not be located initially exactly in register with the anus 22, the swelling of the first and second chamber portions 24, 26 can displace the stem 28a to correct its position such that the waist 25 automatically locates in the anus 22 as the first and second chamber portions 24, 26 swell up internally and externally.

Figure 3:
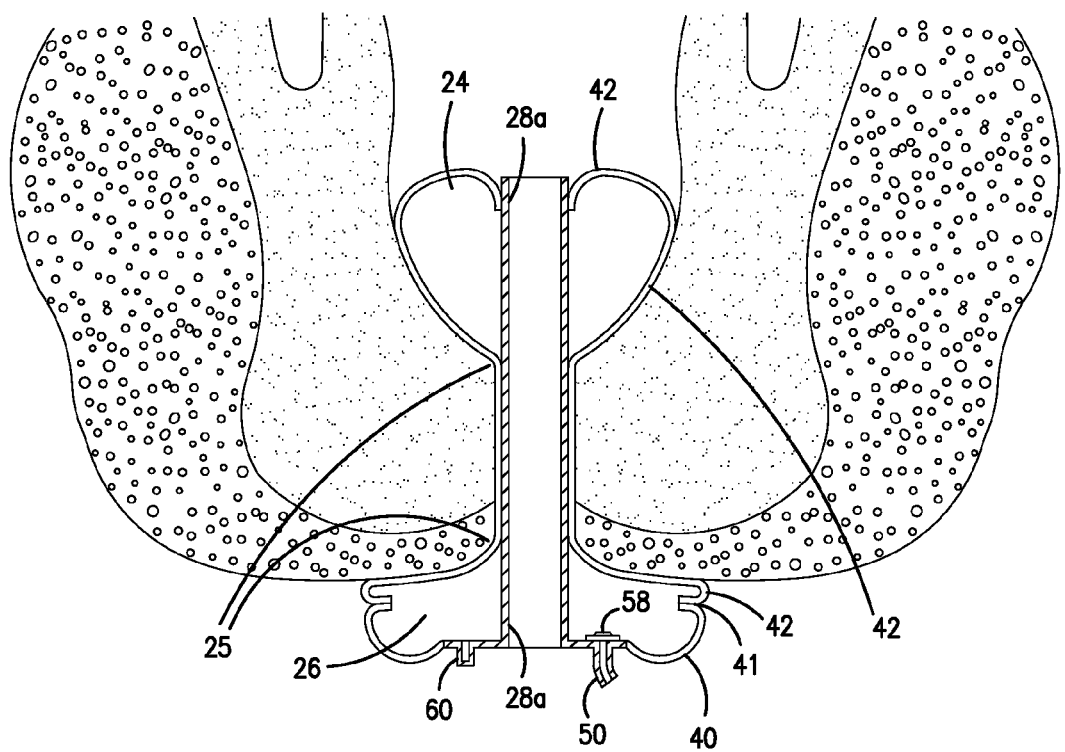
FIG. 3 is a schematic sectional view of the rectal appliance of FIG. 1 in an inflated condition.

As can be seen in FIG. 3, the first and second chamber portions 24, 26 swell to form a conformable, large area seal against the inner wall of the rectum, and against the perianal skin 27. This can achieve a reliable, conformable and comfortable seal, without substantially restricting the mobility of the wearer, and with less risk of the seal being affected by the wearer's movements. Despite the large seal area of the second inflatable chamber portion 26, the external profile of the second inflatable chamber portion 26 may be extremely low, as a result of one or more of:

(a) the seam 41 between the flexible membrane 42 and the rear wall 40 may constrain the shape such that, in the region of the seam 41, the second inflatable chamber portion 26 may expand like a pouch, instead of like a bulbous balloon;

(b) the base 28b of the support 28 may have a molded shape, which may be generally flat, which may prevent substantial rearward bulging of the second inflatable chamber portion 26; and (c) the second inflatable chamber portion 26 may have a generally flared and/or trumpet and/or umbrella type shape and/or a shape having a concave sealing surface portion and/or conform to the shape of the body, which may provide a large sealing area with a generally low projecting height.

The first inflatable chamber portion 24 may also have a flared shape, such that both inflatable chamber portions 24, 26, in use, taper towards (or flare away from) the waist 25. Such a shape can aid self-location of the rectal appliance 20 as the inflatable chambers 24, 26 swell up. In another embodiment the first inflatable chamber portion 24 may have sufficient material so when inflated the first inflatable chamber portion 24 forms a closure in front of the distal end 48 of the stem 28a as shown in FIG. 4. This closure may be opened to discharge waste by partially deflating and/or reducing the pressure within the device but retain enough to maintain the device in place.

An additional or external device (not shown) may be integrated in, or coupled to, the rectal appliance 20 for managing the discharge of body waste through the rectal appliance 20 (for example, by blocking the communication passage 30 in the stem 28a, and/or by collecting the discharge body waste, and/or by allowing the venting of flatus). It will be appreciated that the rectal appliance 20 may allow the discharge of body waste through the communication passage 30 without having to remove the rectal appliance 20 from the anus 22. The rectal appliance 20 may therefore be worn in position for an extended period, thereby avoiding the inconvenient and unhygienic procedure of removing the rectal appliance 20 for each discharge of body waste.

When it is desired to remove the rectal appliance 20 from the anus 22, the user may deflate one or both of the inflatable chambers 24, 26 in any of a number of different ways. For example, the user may puncture one or both of the first and second chamber portions 24, 26, or manipulate the inflation port 50 to vent the inflation fluid. Alternatively, the user may operate a dedicated deflation port 60. The deflation port 60 may, for example, be a break or tear open port. Such a deflation port 60 may ensure that the rectal appliance 20 should not be re-used after it is removed, for example, for reasons of hygiene or for rated life of the components of the rectal appliance 20.

Modifications may be made to these preferred embodiments and still remain within the scope of the claimed invention.

I claim:

1. A rectal appliance comprising:
    a tubular member defining a communication passage for body waste;
    a membrane carried on said tubular member, said membrane at least partly defining:
    (i) a first inflatable chamber portion for forming an internal seal against internal tissue of the anus;
    (ii) a second inflatable chamber portion for forming an external seal against perianal tissue;
    wherein at least a portion of the membrane is fixed relative to said tubular member at an intermediate position intermediate the ends of the tubular member to define a narrow waist region between the first and second inflatable chamber portions; and
    (iii) a plurality of corrugated inflatable columns intermediate the ends of the tubular member, defining passageways for inflation fluid and pathways for escape of flatus.

2. The rectal appliance according to claim 1, wherein said fixation of the membrane relative to the tubular member at said intermediate position is such as to define said passageways for inflation fluid between the first and second inflation chamber portions and pathways for escape of flatus.

3. The rectal appliance according to claim 2, wherein at said intermediate position, the membrane is secured by a discontinuous seal defining said corrugated inflatable columns.

4. The rectal appliance according to claim 1, wherein the tubular member is supported at least partly by said corrugated inflatable columns.

5. The rectal appliance according to claim 1, wherein, in use, at least one of the first and second chamber portions has a generally flared shape extending from the waist.

6. The rectal appliance according to claim 5, wherein both inflatable chamber portions have a respective flared shape.

7. The rectal appliance according to claim 1, wherein the tubular member comprises a flange at or near one end thereof.

8. The rectal appliance according to claim 7, further comprising a closed loop shape flexible or elastic wall connecting the membrane to the flange.

9. The rectal appliance according to claim 8, wherein the closed loop shape flexible or elastic wall provides a volumetric reserve and/or an elastic rebound to the device.

10. The rectal appliance according to claim 1, further comprising an inflation port for inflating the first and second chambers in common.

11. The rectal appliance according to claim 1, further comprising a dedicated deflation port for deflating at least one of the first and second chambers.

12. The rectal appliance according to claim 1, wherein the first inflatable chamber portion has a closed loop shape and is located around the tubular member, for sealing against internal tissue.

13. The rectal appliance according to claim 12, wherein said tubular member has a distal end, and the first inflatable chamber portion is predeterminedly dimensioned so when inflated the first inflatable chamber portion forms a closure in front of the distal end of the tubular member.

14. The rectal appliance according to claim 13, wherein the closure is openable to discharge waste by partially deflating and/or reducing the pressure within the first inflatable chamber portion while retaining enough pressure to maintain the appliance in place.

15. A rectal appliance comprising:
    a tubular member defining a communication passage for body waste; and an external inflatable chamber portion of closed loop shape located around the tubular member, for sealing against perianal skin, the external inflatable chamber portion being defined at least partly by a flexible membrane and a flexible or elastic rear wall that are mutually attached together along a seam of closed loop shape and, a plurality of inflatable columns intermediate the ends of the tubular member, defining passageways for inflation fluid and;

an internal inflatable chamber portion of closed loop shape located around the tubular member, for sealing against internal tissue.

16. The rectal appliance according to claim 15, wherein the seam at least partly constrains the inflated shape of the external inflatable chamber portion.

17. The rectal appliance according to claim 15, further comprising a flange at or near an end of the tubular member, and wherein the flexible or elastic rear wall connects the membrane to the flange.

18. The rectal appliance according to claim 15, wherein the flexible or elastic rear wall has a different material characteristic from the membrane, said different material characteristic including one or more of: different material; different thickness; different flexibility; different elasticity; different resistance to punctures.

19. A rectal appliance comprising:

a tubular member defining a communication passage for body waste, and carrying a flange at or near one end;

an external inflatable chamber portion of closed-loop shape and located around the tubular member, for sealing against perianal skin, the external inflatable chamber portion having a shape defined at least partly by the flange and a plurality of corrugated inflatable columns intermediate the ends of the tubular member defining passageways for inflation fluid and pathways for escape of flatus and;

an internal inflatable chamber portion of closed loop shape extending around the tubular member, for sealing against internal tissue.

20. The rectal appliance according to claim 19, wherein the external inflatable chamber portion comprises at least one flexible wall supported by the flange.

21. The rectal appliance according to claim 20, wherein the external inflatable chamber portion further comprises a flexible membrane coupled to the flexible wall, and wherein the flexible wall is coupled to the flange.

* * * * *